United States Patent [19]

Iwamoto et al.

[11] Patent Number: 4,657,540

[45] Date of Patent: Apr. 14, 1987

[54] HIGH PRESSURE STEAM STERILIZED PLASTIC CONTAINER HOLDING INFUSION SOLUTION AND METHOD FOR MANUFACTURING THE SAME

[75] Inventors: Tomiyuki Iwamoto, Tokyo; Naoki Hayakawa, Kashiwa; Shigeru Matsubara, Tokyo, all of Japan

[73] Assignee: Terumo Corporation, Tokyo, Japan

[21] Appl. No.: 757,770

[22] Filed: Jul. 23, 1985

Related U.S. Application Data

[63] Continuation of Ser. No. 384,190, Jun. 3, 1982, abandoned.

[30] Foreign Application Priority Data

Jun. 12, 1981 [JP] Japan ................... 56-90392

[51] Int. Cl.$^4$ .............................................. A61B 19/00
[52] U.S. Cl. ...................... 604/408; 422/25; 604/46
[58] Field of Search ................. 604/46, 262, 408–410; 128/DIG. 4; 426/412, 512; 422/25

[56] References Cited

U.S. PATENT DOCUMENTS 3,064,652  11/1962  Corcoran et al. ................... 604/408
4,334,535  6/1982   Wilson et al. ............. 128/DIG. 24
4,453,940  6/1984   Aoyagi ................................ 604/408

FOREIGN PATENT DOCUMENTS 1933542  6/1971  Fed. Rep. of Germany.
2363468  7/1975  Fed. Rep. of Germany.
2800484  7/1978  Fed. Rep. of Germany.
2933071  3/1980  Fed. Rep. of Germany.

OTHER PUBLICATIONS

The Condensed Chemical Dictionary, 1981, p. 561.

*Primary Examiner*—C. Fred Rosenbaum
*Assistant Examiner*—Sherri E. Vinyard
*Attorney, Agent, or Firm*—Frishauf, Holtz, Goodman & Woodward

[57] ABSTRACT

A high pressure steam sterilized plastic container holding an infusion solution therein is prepared first by providing a flexible container made of plastic material and holding an infusion solution. The container is then sterilized in a saturated steam atmosphere which is pressurized by a gas inert to the infusion solution and does not contain oxygen. The infusion solution in the container is not deteriorated after the sterilization.

21 Claims, 3 Drawing Figures

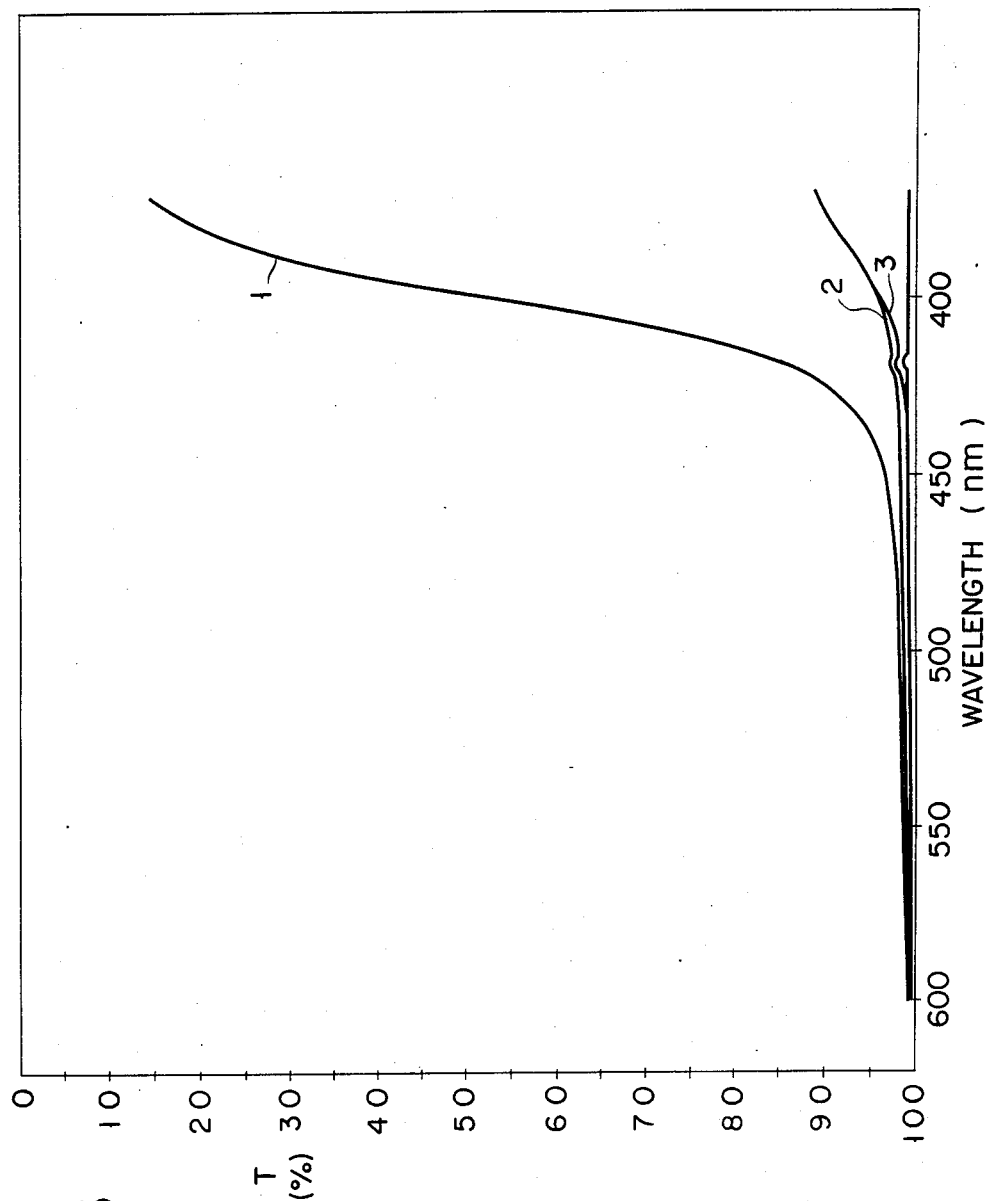

HIGH PRESSURE STEAM STERILIZED PLASTIC CONTAINER HOLDING INFUSION SOLUTION AND METHOD FOR MANUFACTURING THE SAME

This application is a continuation of application Ser. No. 384,190 filed June 3, 1982, now abandoned.

BACKGROUND OF THE INVENTION

I. Field of the Invention

The present invention relates to a high pressure steam sterilized plastic container holding an infusion solution and to a method for manufacturing the same.

II. Description of the Prior Art

In an attempt to prevent infection by administration of an injection infusion at a hospital, a closed system which does not use an air needle has been recently proposed. In order to provide such a closed system, a flexible plastic container must be used as a container holding an infusion solution in place of a conventional glass bottle or ampoule. This is because fluid therapy in a closed system utilizes flexibility of the container.

Such a plastic container holding an infusion solution must be sterilized before fluid therapy as in the prior art. Sterilization is most commonly performed by high pressure steam sterilization which utilizes saturated steam at a high temperature. However, a plastic material, such as polyvinyl chloride, which has a low permeability to gases will have a high permeability to gases during sterilization in a high pressure steam. Then, oxygen in the atmosphere permeates the container wall to deteriorate the infusion solution therein. Such deterioration of the infusion solution presents a big problem if the infusion solution contains components, such as a fat emulsion or a concentrated amino acid solution containing tryptophane, which are easily subject to deterioration upon contact with oxygen. Furthermore, a flexible container may be damaged under the normal high pressure steam sterilization conditions.

SUMMARY OF THE INVENTION

It is an object of the present invention to provide a high pressure steam sterilized plastic container which holds an infusion solution which has not been deteriorated by sterilization and to a method for manufacturing the same.

In order to achieve this object, there is provided according to the present invention a high pressure steam sterilized plastic container holding an infusion solution, comprising a flexible container of a plastic material and the infusion solution held therein, the container being sterilized in a saturated steam atmosphere which is pressurized by a gas inert to the infusion solution and which contains substantially no oxygen, so that the infusion solution is not substantially deteriorated after sterilization.

The wall of the container is preferably made of polyvinyl chloride or a cross-linked ethylene-vinyl acetate copolymer (to be referred to as an EVA copolymer for brevity hereinafter). Although the EVA copolymer is preferable from the viewpoint of purity since it does not contain a plasticizer, it has a low heat resistance. In order to improve the heat resistance of the EVA copolymer, it is necessary to irradiate the EVA copolymer with an electron beam or the like to obtain a gel content of 50% or more. In order to obtain satisfactory flexibility, the container wall preferably contains vinyl acetate in the amount of 10 to 35% by weight.

The present invention is particularly advantageous where the infusion solution contains at least one component which is easily deteriorated upon contact with oxygen. Examples of such components are parenteral nutrition components such as a fat emulsion and a concentrated amino acid solution containing tryptophane.

The plastic container holding an infusion solution of the present invention is manufactured by preparing a flexible container of a plastic material holding the infusion solution, and sterilizing the container in a saturated steam atmosphere which is pressurized by a gas inert to the infusion solution and which does not substantially contain oxygen.

The sterilization temperature is usually selected to be 100° to 130° C. and preferably 115° to 126° C.

The saturated steam pressure at the sterilization temperature is generally increased by the inert gas by about 10 to 200%. The sterilization atmosphere pressure (gauge pressure) is preferably 1.2 to 2.0 kg/cm$^2$. The inert gas is preferably nitrogen.

When the container is cooled after sterilization, it is preferable to pressurize the interior of the container by the inert gas in order to maintain the pressure during sterilization. The plastic container holding the infusion solution manufactured in this manner is conveniently packed with a gas-impermeable packing material.

According to the present invention, a flexible plastic container which is sterilized and which holds an infusion solution which is not deteriorated is readily provided.

BRIEF DESCRIPTION OF THE DRAWINGS

FIG. 3 is a graph showing transmittance T (%) of the infusion solution which is sterilized according to the present invention as a function of wavelength (nm).

DETAILED DESCRIPTION OF THE PREFERRED EMBODIMENTS

The preferred embodiments of the present invention will now be described with reference to the accompanying drawings.

Figure 1:
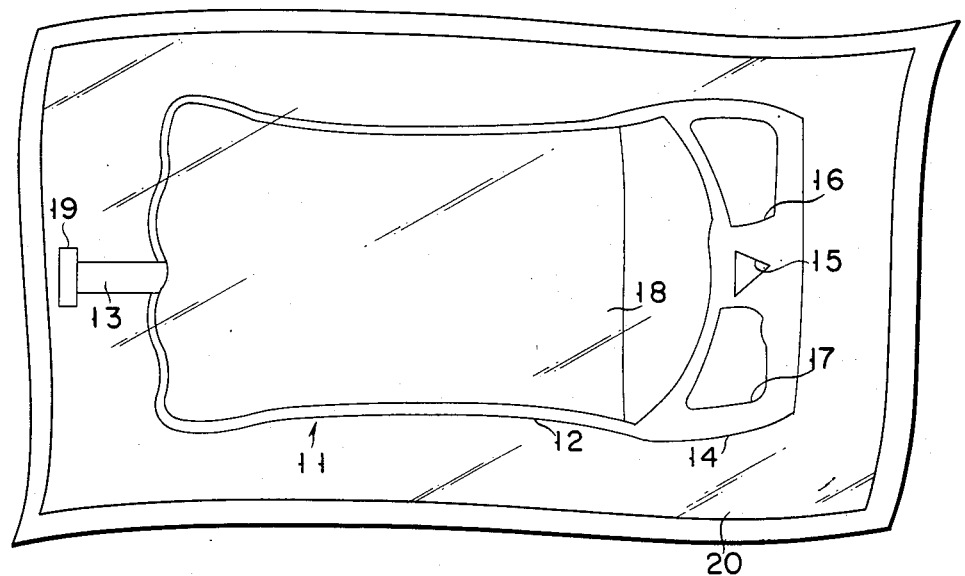
FIG. 1 is a plan view of a plastic container holding an infusion solution packed with a gas-impermeable packing material, according to the present invention.

As shown in FIG. 1, a plastic container holding an infusion solution of the present invention has a flexible container 11. The container 11 is made of a plastic material having a high heat resistance such that it can withstand the steam sterilization. Such material includes polyvinyl chloride, a cross-linked EVA copolymer, or a high-density polyethylene. The container 11 may be prepared by stacking two sheets of such a plastic material and adhering peripheries 12 of these sheets under heating. If the sheets are made of an EVA copolymer, it is preferable to prepare a container body in the manner to be described above and to cross-link it with an electron beam or the like such that the gel content of the copolymer is 50% or more. The gel content is defined as the weight of the cross-linked EVA copolymer after sufficient extraction with a good solvent such as hot xylene divided by the weight before the extraction.

The container 11 has at its one end an infusion solution port 13. The container 11 has at its other end a relatively wide region 14. Within the region 14, a suspension hole 15 for suspending the container 11 and through holes 16 and 17 for other purposes are formed.

An infusion solution 18 is fed into the container 11. The infusion solution 18 may contain components which are easily deteriorated upon contact with oxygen. Examples of such components include the total parenteral nutrition components such as a fat emulsion or a concentrated (generally 10 to 12%) amino acid solution containing tryptophane. After filling the container 11 with the infusion solution 18, the port 13 is closed with a sealing member 19 by thermal sealing, high-frequency adhesion or the like.

After high pressure steam sterilization, the plastic container holding the infusion solution according to the present invention is preferably packed with a packaging material 20. Preferably the material 20 is a laminate film having a biaxially stretched polypropylene film as an outer film, an ethylene-vinyl alcohol copolymer film as an intermediate film, and a monoaxially stretched polypropylene film as an inner layer. Then, the container is not brought into contact with the ambient air after sterilization, and deterioration of the infusion solution held therein is prevented over a long period of storage time. In order to reduce the amount of air remaining in the package to the minimum, it is preferable to vacuum-pack the container 11 with the packaging material 20. More preferably, a deoxidizer (not shown) is also sealed within the package. The deoxidizer serves to absorb oxygen which may be present in the package and prevents deterioration of the infusion solution 18 due to oxidation during storage.

Figure 2:
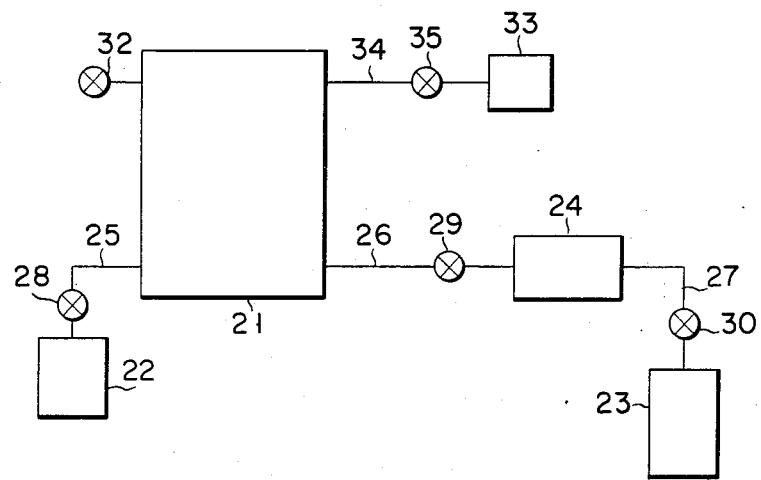
FIG. 2 is a schematic view of a high pressure steam sterilizing apparatus used according to the present invention.

The container 11 holding the infusion solution 18 is sterilized by a high pressure sterilizing apparatus shown in FIG. 2. This apparatus has an autoclave 21 for sterilization. One end of the autoclave 21 is connected to a steam source such as a boiler 22 through a line 25 via a valve 28. An inert gas source 23 is connected to the autoclave 21 through a line 27, a valve 30, an inert gas reservoir 24, a line 26, and a valve 29. Further, an exhaust valve 32 is connected to the autoclave 21. The inert gas reservoir 24 need not be incorporated. If the inert gas reservoir 24 is omitted, the line 26 and the valve 29 can also be omitted. A cooling water source 33 is also connected to the autoclave 21 through a line 34 and a valve 35.

For sterilization, a plurality of plastic containers holding the infusion solution are placed in the autoclave 21. Steam is introduced into the interior of the autoclave 21 for a predetermined period (e.g., 2 to 10 minutes) to substantially remove air or oxygen therein from the exhaust valve 32. Then, the valve 32 is closed, and steam at a predetermined temperature from the boiler 22 is introduced into the autoclave 21 until it fully fills the autoclave 21, and the valve 28 is closed. An inert gas such as argon, helium or nitrogen (most preferable) from the inert gas reservoir 24 which is used for stocking of the inert gas from the inert gas source 23 is introduced into the autoclave 21 to pressurize the interior of the autoclave 21. After closing the valve 29, sterilization is performed. The sterilization temperature is generally kept within the range of 100° to 130° C. and preferably within the range of 115° to 126° C. In order to obtain the satisfactory results, the sterilization atmosphere pressure is increased to a pressure (e.g., about 0.3 to 0.8 kg/cm$^2$) about 10 to 200% greater than the saturated steam pressure at the sterilization temperature. Conventionally, the pressure during sterilization is regulated and is about 1.2 to 2.0 kg/cm$^2$ in gauge pressure. The sterilization time is suitably selected to be 10 to 40 minutes. The inert gas is supplemented through the valve 29 during sterilization to keep the predetermined pressure.

After sterilization, a predetermined amount of cooling water from the cooling water source 33 is introduced into the autoclave 21 through the line 34. During cooling, the internal pressure inside the autoclave 21 relatively rapidly decreases. For this reason, the container may be damaged due to the pressure of the infusion solution which is still hot. In order to prevent this, it is preferable to open the valve 29 as the cooling water is introduced into the autoclave 21 to introduce the inert gas into the autoclave 21 and to maintain the internal pressure of the autoclave 21 substantially the same as that during sterilization. After the infusion solution within the container is cooled well, the gas within the autoclave 21 is discharged through the exhaust valve 32 to place the interior of the autoclave 21 at normal atmospheric pressure.

The present invention will now be described in further details by way of examples.

EXAMPLE 1

A 12% amino acid solution (containing tryptophane) was prepared according to the conventional method and filled in a container made of a soft polyvinyl chloride resin. Some samples of containers filled with the infusion solution in this manner were prepared. After placing these containers in a retort-type sterilizer, sterilization was performed at a temperature of 117° C. and a gauge pressure of 1.8 kg/cm$^2$ for 37 minutes. In order to maintain the interior of the sterilizer at the pressure mentioned, saturated steam was pressurized by nitrogen gas. After sterilization was completed, the inert gas was introduced into the autoclave during cooling to maintain the interior of the sterilizer at the same pressure as that during sterilization. In this manner, each container was sterilized without any damage. Table 1 shows sterile states of the 12% amino acid solution with those obtained by the conventional sterilization method.

TABLE 1

| Test Item | Before Sterilization | After Sterilization | |
|---|---|---|---|
| Appearance[1] | Colorless and Transparent | Prior Art | Pale Yellow and Transparent |
| | | Present Invention | Colorless and Transparent |
| pH[2] | 5.89 | Prior Art | 5.90 |
| | | Present Invention | 5.89 |
| Dissolved Oxygen (ppm)[3] | 1.8 | Prior Art | 4.8 |
| | | Present Invention | 0.6 |

Note:
[1]Samples were filled in Nessler tubes in amounts of 30 mm each and were compared with distilled water with naked eyes.
[2]The pH was measured with a pH meter (HM-6A) manufactured by Toa Denki K.K.
[3]Dissolved oxygen was measured with a DO meter (DO-3) manufactured by Denki Kagaku Keiki K.K.

FIG. 3 is a graph showing light transmittance curves of the 12% amino acid solution within a wavelength range of 600 to 370 nm. The transmittance was measured with a spectrophotometer (200-20 type manufactured by Hitachi, Ltd.) Curve 1 represents the transmittance after sterilization according to the conventional method. Curve 2 represents the transmittance after sterilization according to the present invention. Curve 3 represents the transmittance before sterilization.

EXAMPLE 2

Refined soy oil, egg yolk lecithin and glycerin were emulsified in distilled water for injection to prepare a fat emulsion which contained refined soy oil in the amount of 10%. The fat emulsion was filled in flexible containers of a cross-linked EVA copolymer. These containers were sterilized in the same manner as in Example 1 except that the sterilization time was 30 minutes. No damage to the containers was observed. Table 2 shows the characteristics of the fat emulsion after sterilization together with those of the fat emulsion after sterilization according to the conventional method.

TABLE 2

| Test Item | Before Sterilization | After Sterilization | |
|---|---|---|---|
| Appearance[1] | White, Non-transparent | Prior Art | Slightly Colored |
| | | Present Invention | White, Non-transparent |
| pH[2] | 7.78 | Prior Art | 7.52 |
| | | Present Invention | 7.75 |
| Dissolved Oxygen (ppm)[3] | 0.3 | Prior Art | 6.5 |
| | | Present Invention | 0.3 |
| Acid Value[4] | 0.245 | Prior Art | 0.253 |
| | | Present Invention | 0.247 |

Note:
[1]Emulsions in the containers were observed with the naked eye
[2],[3]Same as in Example 1.
[4]The acid value was measured according to the ninth amended fat test method of Japanese Pharmacopeia.

Although the present invention has been described with reference to particular embodiments, the present invention is by no means limited to this. For example, the infusion solution is not limited to the total parenteral nutrition components but may be elemental diet components for oral administration. Although these elemental diet components need not be sterilized, they may be stored without deterioration over a long period of time if they are sterilized according to the method of the present invention.

According to the present invention, a flexible plastic container (e.g., heat-resistant polyvinyl chloride or cross-linked EVA copolymer) holding an infusion solution is sterilized in a saturated steam atmosphere (at a gauge pressure of 1.2 to 2.0 kg/cm$^2$) which is pressurized with the inert gas and which does not substantially contain oxygen and at a high temperature such as 100° to 130° C. Since the inert gas is introduced, deterioration of the infusion solution due to oxidation may be substantially prevented. Since sterilization is performed at a predetermined pressure, damage to the container due to expansion of the infusion solution may also be prevented. Accordingly, the container of the present invention is most conveniently used as a plastic container for holding an infusion solution containing components which are easy to deteriorate upon contact with oxygen such as a fat emulsion and a concentrated amino acid solution containing tryptophane. When the container wall is particularly preferably made of the cross-linked EVA copolymer, the heat-resistance of the cross-linked EVA copolymer is excellent and does not produce any elute.

In summary, the present invention provides a flexible plastic container which is sterilized and which holds an infusion solution which is not deteriorated.

What we claim is:

1. A high pressure steam sterilized plastic container holding an infusion solution, comprising:
   a flexible container of a plastic material,
   an infusion solution contained in said flexible container, said infusion solution containing at least one component which is deteriorated substantially upon contact with oxygen, said infusion solution being selected from the group consisting of a concentrated amino acid solution containing tryptophane and a fat emulsion, and
   a gas-impermeable package made of gas-impermeable material and within which said flexible container with said infusion solution therein is contained after sterilization of said flexible container, said gas-impermeable package preventing deterioration of said infusion solution over a period of time,
   the container being sterilized with said infusion solution contained therein, by:
   placing said container with said infusion solution therein in a substantially oxygen-free sterilization atmosphere consisting essentially of saturated steam and nitrogen gas which is inert to said infusion solution, said nitrogen gas pressurizing said saturated steam so that said container with said infusion solution therein is sterilized in said sterilization atmosphere without substantially deteriorating said infusion solution in said container.

2. A container according to claim 1, wherein a wall of the container is made of a member selected from the group consisting of polyvinyl chloride and an ethylene-vinyl acetate copolymer.

3. A container according to claim 1, wherein said gas-impermeable material is a laminate film having a polypropylene film as an outer film, an ethylene-vinyl alcohol copolymer film as an intermediate film, and a polypropylene film as an inner film layer of said gas-impermeable package.

4. A method for manufacturing a high pressure steam sterilized plastic container holding an infusion solution therein, comprising the steps of:
   preparing a flexible container of a plastic material holding the infusion solution therein;
   placing said container with said infusion solution therein in a substantially oxygen-free sterilization atmosphere consisting essentially of saturated steam and nitrogen gas which is inert to said infusion solution, said nitrogen gas pressurizing said saturated steam whereby said container with said infusion solution therein is sterilized in said sterilization atmosphere without substantially deteriorating said infusion solution in said container; and
   packaging said flexible container in a gas-impermeable package which is made of a packaging material which is impermeable to gases, to thereby prevent deterioration of said infusion solution over a period of time.

5. A method according to claim 4, wherein the infusion solution contains at least one component which easily deteriorates upon contact with oxygen.

6. A method according to claim 5, wherein the infusion solution is at least one total parenteral nutrition component.

7. A method according to claim 6, wherein the infusion solution is a concentrated amino acid solution containing tryptophane.

8. A method according to claim 6, wherein the infusion solution is a fat emulsion.

9. A method according to claim 5, further comprising the step of cooling the container after sterilization.

10. A method according to claim 9, wherein sterilization is performed in an autoclave.

11. A method according to claim 10, wherein nitrogen gas is introduced into the autoclave for maintaining the interior of the autoclave at the pressure during sterilization.

12. A method according to claim 11, wherein cooling is performed by introducing water into the autoclave.

13. A method according to claim 4, wherein a sterilization temperature is 100° to 130° C.

14. A method according to claim 13, wherein the infusion solution contains at least one component which easily deteriorates upon contact with oxygen.

15. A method according to claim 4, wherein a saturated steam at the sterilization temperature is pressurized by the nitrogen gas by about 10 to 200%.

16. A method according to claim 15, wherein the infusion solution contains at least one component which easily deteriorates upon contact with oxygen.

17. A method according to claim 4, wherein a sterilization temperature is 115° to 126° C. and an atmosphere pressure is 1.2 to 2.0 kg/cm$^2$ in a gauge pressure.

18. A method according to claim 17, wherein the infusion solution contains at least one component which easily deteriorates upon contact with oxygen.

19. A method according to claim 4, wherein a wall of the container is made of a member selected from the group consisting of polyvinyl chloride and an ethylenevinyl acetate copolymer.

20. A method according to claim 19, wherein the infusion solution contains at least one component which easily deteriorates upon contact with oxygen.

21. A method according to claim 4, wherein said gas-impermeable material is a laminate film having a polypropylene film as an outer film, an ethylene-vinyl alcohol copolymer film as an intermediate file, and a polypropylene films as an inner film layer of said gas-impermeable package.

* * * * *